United States Patent
Crank et al.

(10) Patent No.: US 6,530,912 B2
(45) Date of Patent: Mar. 11, 2003

(54) APPARATUS FOR CONNECTING A COMPATIBILITY LINER WITH A SOURCE OF PERISHABLE THERAPEUTIC

(75) Inventors: Justin M. Crank, Elk River, MN (US); Timothy A. Ostroot, South Haven, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/758,129

(22) Filed: Jan. 12, 2001

(65) Prior Publication Data
US 2002/0095136 A1 Jul. 18, 2002

(51) Int. Cl.[7] .............. A61M 25/00; A61M 31/00; A61M 5/32; A61M 5/00
(52) U.S. Cl. .............. 604/523; 604/533; 604/534; 604/535; 604/539; 604/177; 604/264; 604/522; 604/93.01
(58) Field of Search ............ 604/93.01, 177, 604/264, 523, 533–535, 539, 522

(56) References Cited

U.S. PATENT DOCUMENTS

| | | | | |
|---|---|---|---|---|
| 3,720,210 A | * | 3/1973 | Diettrich .................. 128/214.4 |
| 4,354,495 A | * | 10/1982 | Bodicky .................. 128/348 |
| 4,391,029 A | * | 7/1983 | Czuba et al. .................. 29/450 |
| 4,976,703 A | | 12/1990 | Franetzki et al. ........... 604/247 |
| 5,098,410 A | * | 3/1992 | Kerby et al. .................. 604/256 |
| 5,695,479 A | * | 12/1997 | Jagpal ........................ 604/264 |
| 5,702,372 A | | 12/1997 | Nelson ........................ 604/264 |
| 5,746,694 A | | 5/1998 | Wilk et al. .................. 600/123 |
| 5,782,797 A | * | 7/1998 | Schweich, Jr. et al. ....... 604/49 |
| 5,795,324 A | * | 8/1998 | Morse ........................ 604/27 |
| 5,817,072 A | * | 10/1998 | Lampropoulos et al. .... 604/264 |

* cited by examiner

Primary Examiner—Timothy L. Maust
Assistant Examiner—Anuradha Ramana
(74) Attorney, Agent, or Firm—Kenyon & Kenyon

(57) ABSTRACT

An apparatus for connecting a compatibility liner with a source of perishable therapeutic is provided. In one exemplary system for connecting a reservoir of perishable therapeutic with a lumen, a hollow hub having a first end and a second end is provided. The first end of the hollow hub, which contains a bond port, is in fluid communication with the second end. The second end of the hollow hub may contain a docking groove that is sized to couple a reservoir to it. The system also includes an inner hypo-tube having a proximal tip and an inner lumen. This inner lumen is lined with a therapeutic compatible lining and is in fluid communication with the second end of the hub through the proximal tip of the inner hypo-tube. The inner lining and the proximal tip in this system are configured to shield therapeutic ejected from the reservoir from contacting materials that can diminish the integrity of the therapeutic.

12 Claims, 5 Drawing Sheets

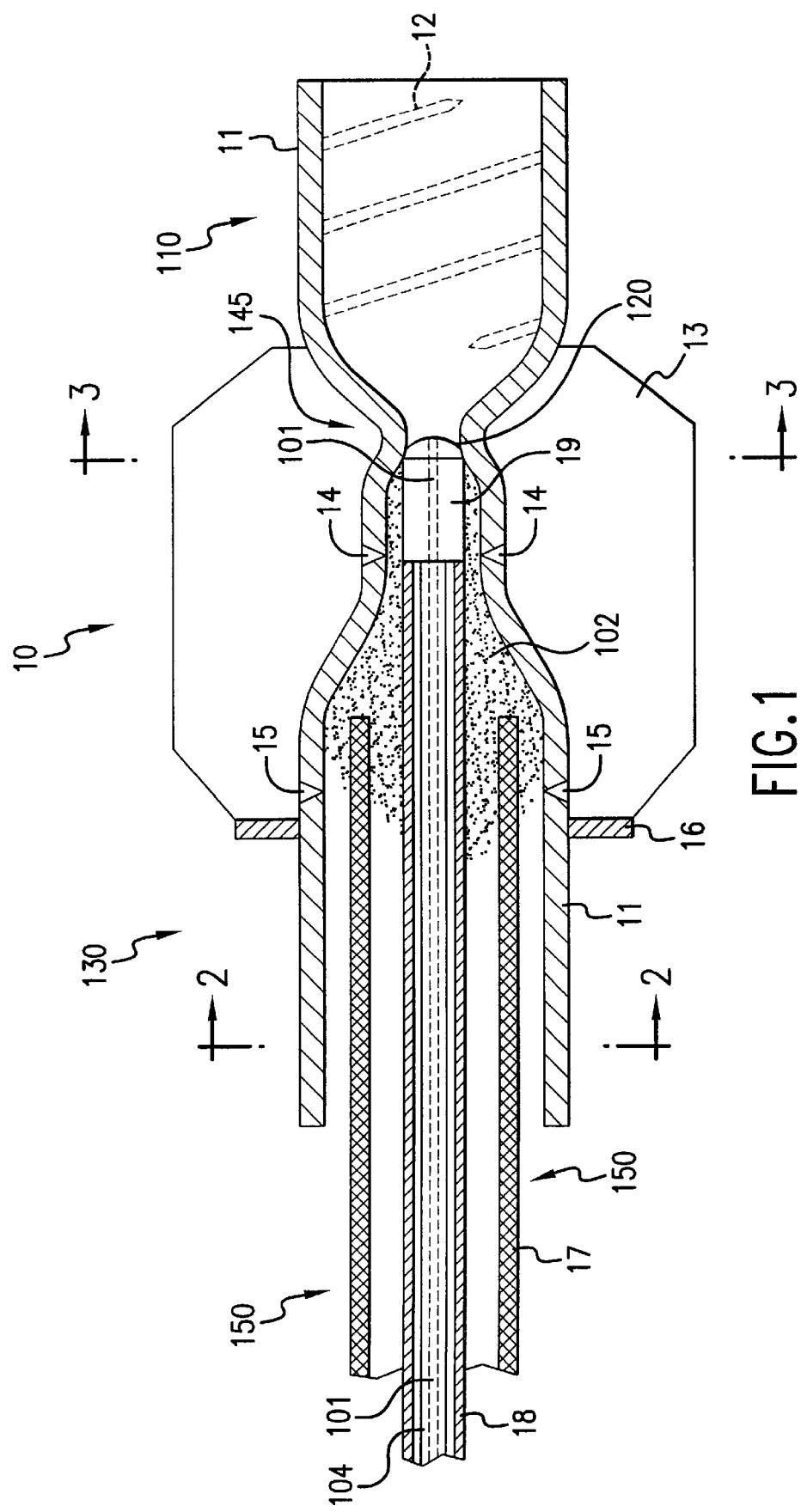

APPARATUS FOR CONNECTING A COMPATIBILITY LINER WITH A SOURCE OF PERISHABLE THERAPEUTIC

FIELD OF THE INVENTION

The present invention relates to the transport of perishable therapeutics from a storage reservoir to a target site. More specifically the present invention relates to method and apparatus for effectively connecting a reservoir of perishable therapeutic to a lumen that is lined with a material compatible with the perishable therapeutic.

BACKGROUND OF THE INVENTION

The delivery of therapeutics to a target site in the body of a patient is a task that finds innumerable applications in the practice of modern medicine. In some application the therapeutic may be delivered through a needle and while in others the therapeutic may be delivered though a pump and catheter system. In either of these configuration, as with the many other plausible configurations, the objective is to deliver active therapeutic to a target site such that the therapeutic may cure the infirmities resident at the target site. For some perishable, sensitive or volatile therapeutic, such as certain viruses employed today, a compatibility issue can arise between the therapeutic and the channel or vessel that will transport the therapeutic from its storage vessel to its target site. When compatibility issues do arise between the therapeutic and its surroundings, the therapeutic may lose some or all of its effectiveness and may, upon its arrival at the target site, be partially or completely inert. In certain applications, the therapeutic may lose its effectiveness moments before it is delivered as it passes down and through the delivery lumen of the delivery device simply because the therapeutic has come in contact with a non-compatible material.

Therefore, the environment in which the therapeutic is stored as well as the environment in which the therapeutic must travel can and does affect the potency and effectiveness of certain perishable therapeutics. In order to avoid the risk of deterioration of the potency of perishable therapeutics it is, consequently, advantageous to minimize or eliminate the contact between non-compatible materials and the therapeutic during the delivery of the therapeutic to the target site.

SUMMARY OF THE INVENTION

The present invention includes the proper handling of perishable therapeutic. In one embodiment a system for connecting a reservoir of perishable therapeutic with a lumen is provided. This embodiment has a hollow hub having a first end and a second end. The first end of the hollow hub, which contains a bond port, is in fluid communication with the second end of the hollow hub. The second end of the hollow hub in this embodiment may contain a docking groove that is sized to couple a reservoir to it. This embodiment also includes an inner hypo-tube having a proximal tip and an inner lumen. The inner lumen may be lined with a perishable therapeutic compatible lining and may be in fluid communication with the second end of the hub through the proximal tip of the inner hypo-tube. The inner lining and the proximal tip may be configured to shield perishable therapeutic, ejected from the reservoir and present within the second end, from materials that are non-compatible with the therapeutic.

In a second embodiment a method for coupling a reservoir of perishable therapeutic to a lumen lined with a therapeutic compatible lining is provided. This method includes inserting the proximal end of a manifold hypo-tube into a first end of a hub, the hub also having a second end; placing the proximal end of an inner hypo-tube within the proximal end of the manifold hypo-tube and urging the proximal end of the inner hypo-tube through the proximal end of the manifold hypo-tube until the proximal end of the inner hypo-tube comes in contact with a stopping point in the hub. In this second embodiment the tip of the proximal end of the inner hypo-tube may be covered in a therapeutic compatible material and the inner surface of the inner hypo-tube may be covered with a therapeutic compatible lining.

BRIEF DESCRIPTION OF THE DRAWINGS

FIG. 1 is a side sectional view of the proximal end of a concentric hypo-tube assembly employed in an embodiment of the present invention.

DETAILED DESCRIPTION

Figure 3:
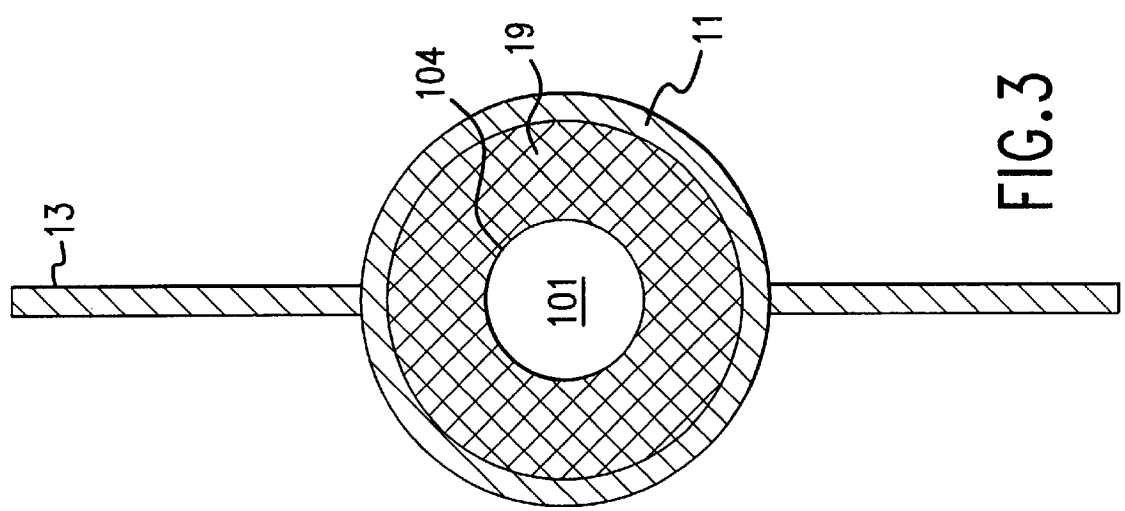
FIG. 3 is a cross-sectional view taken along line 3—3 of FIG. 1.

As described and used herein a "perishable therapeutic" includes a therapeutic whose efficiency can be diminished through the contact with specific non-compatible compounds or materials. These perishable therapeutics include adenoviral vectors; adeno-associated vectors; certain proteins including basic fibroblast growth factors; certain nucleic acids such as DNA plasmid; and, certain cells such as myoblasts, fibroblasts, and stem cells. Thus, regarding these examples, when these perishable therapeutics come in contact with stainless steel, for example, they lose some or all of their effectiveness as a therapeutic. This list of perishable therapeutics is not exhaustive but, instead, is meant to be exemplary of therapeutics that may lose some or all of their healing effectiveness once placed in proximity to a specific non-compatible material.

As described and used herein a "perishable therapeutic compatible lining" includes a lining that does not substantially retard the effectiveness of an otherwise perishable therapeutic. It may include a specific coating applied to a material as well as a separate material that is later adhered or placed adjacent to the underlying material that it lines. One primary purpose of this lining is to retard the degradation of therapeutic that comes in contact with it. While the lining may modify the effectiveness of the therapeutic it does so at a lesser rate than that of the material that it covers and would otherwise come in contact with the therapeutic.

As described and used herein "non-compatible" is an adjective used to describe materials that more than insubstantially affect the potency or effectiveness of a therapeutic. When quantified this may include materials that reduce a therapeutic's efficiency by approximately 10% through and including an entire 100% reduction in its effectiveness, thereby making the use of the therapeutic, after coming in contact with the non-compatible material, an inconsequential event.

FIG. 1 is a side sectional view of a concentric hypo-tube assembly 150 and hub 10 in accordance with one embodiment of the present invention. In FIG. 1 the hub 10 and the proximal end of the concentric hypo-tube assembly 150 are clearly evident. As can be seen the hub 10 may be shaped in the form of an hour-glass with a longer end 130 connected to a female luer connection 110 through a channel 145 having a stopping point 120. The hub 10 in FIG. 1 contains a hub wall 11 which may be manufactured from a single material such as a polypropylene, a polycarbonate or any other material that is rigid and compatible with the perishable therapeutics that may be delivered by the hypo-tube assembly 150. Alternatively, should this material not be compatible with the therapeutic it may be lined with a material that is.

As can be seen, the female luer connection 110 contains threads or grooves 12, which are illustrated in FIG. 1 as angled dashed lines encircling the interior surface of the female luer connection 110. These grooves 12 and the female luer connection 110 may be dimensioned so as to accept and secure a removable reservoir (which is not shown) containing perishable therapeutic. This perishable therapeutic may be injected down through the concentric hypo-tube assembly 150 to a target site within the body by depressing a syringe (not shown) integrated with the removable reservoir. As can be seen, a threaded reservoir containing the therapeutic may be readily attached to the female luer connection 110 by aligning and screwing the reservoir into the connection 110.

As is evident the proximal end of a manifold hypo-tube 17 and the proximal end of an inner hypo-tube 18 are located within the longer end 130 of the hub 10. The manifold hypo-tube 17 and the inner hypo-tube 18 may be designed for numerous medical applications. They may be designed to be part of an injection catheter used to inject perishable therapeutic into the heart or other dense tissue area of a patient. They may also be designed to be implanted in the body and used for long-term delivery of a therapeutic. When used for puncturing applications the hypo-tubes may be made from stainless steel or other suitably rigid materials. Conversely, when used in less stress-intensive applications the hypo-tubes may be made from less rigid materials such as plastic.

In this particular embodiment the manifold hypo-tube 17 is made from stainless steel and is attached to a spring mechanism of an injection catheter (not shown) which is used to inject a needle into the heart or cardiopulmonary sac of a patient. Once the needle is injected into the heart or cardiopulmonary sac the inner hypo-tube 18, also stainless steel, would be used to carry therapeutic to the targeted site of the body.

In this embodiment the inner hypo-tube 18 contains a liner 104, which may be made from polyether block-amide (one example of which is Pebax™ 5533) or any other material that is compatible with a perishable therapeutic that may contact the liner 104. The proximal end of the inner hypo-tube 18 in this embodiment has a collar 19 adjacent to it. This collar 19 may be made from the same material as the liner or it may be made from another material as long as the second material is also compatible with the perishable therapeutic that may come in contact with it. The collar 19, made from a therapeutically compatible material, may be sized to compressibly secure or press-fit itself to the stopping point 120 located within the channel 145 of the hub 10. In this embodiment the liner 104 extends out of the inner hypo-tube and through the collar 19 to line the interior lumen of the collar. Therefore, when the inner hypo-tube is being manufactured the liner 104 may be protruding from the proximal end of the hypo-tube and may be covered by or threaded through the collar such that the liner 104 lines the interior lumen of the collar.

In this embodiment the inside diameter of the lumen in the inner hypo-tube 18 may be about 0.0130 inches and the outside diameter of the inner hypo-tube 18 may be about 0.0250 inches. The inside diameter of the liner 104 may be 0.0075 inches. Other sizes and dimensions are also possible.

The stopping point 120 of the hub 10 in this embodiment is sized such that it may snugly secure the collar 19 to the hub 10 after the collar 19 has been pushed or urged toward the stopping point 120. In other words, the use of friction and the proper sizing of the dimensions between the stopping point 120 and the collar 19 create a mechanical adhesion or press-fit that couples the collar 19 to the hub 10 at the stopping point 120 and prevents over-wicking of adhesive 102.

The hub wall 11 also contains a plurality of bond ports. In this figure a first bond port 14 is shown in the channel 145 of the hub 10 while a second bond port 15 is shown on the longer end 130 of the hub 10. These bond ports may have a funnel-like configuration and may provide an access via from outside the hub to inside the hub to allow adhesive or other material to be injected from outside the hub 10 at different points along the hub 10.

In FIG. 1 an adhesive 102 is shown after being injected into the hub 10 through the first bond port 14 and the second bond port 15 to secure the inner hypo-tube 18 and the manifold hypo-tube 17 to each other and to the hub 10. As is evident the adhesive 102 surrounds the proximal end of the inner hypo-tube 18 as well as the proximal end of the manifold hypo-tube 17 but has not wicked past the stopping point 120 between the collar 19 and the hub 10. In practice it is preferred that the amount of adhesive injected into the hub is controlled such that no adhesive wicks past the stopping point 120 and, consequently, risks coming in contact with therapeutic that may be injected down the lumen of the inner hypo-tube. The adhesive employed in this embodiment may be H.B. Fuller adhesive no. 3507 and Tra-con FDA2.

Other features of the hub 10 illustrated in FIG. 1 are the reinforcing nub 16 and the wing 13. These two components extend from the tubular hourglass-designed hub 10 and allow the hub 10 to be grasped and rotated as required. For example, when a threaded reservoir of therapeutic needs to be screwed or coupled into the female luer connection 110 of the hub 10, the wings 13 can be grasped by an operator and used to rotate the hub 10 to couple the hub 10 to the therapeutic reservoir (not shown).

In manufacturing the device illustrated in FIG. 1, a manufacturer may first gather the components to be assembled. These components would include the inner hypo-tube 18, the manifold hypo-tube 17, and the hub 10. As a first step the manufacturer may insert the proximal or near end of the manifold hypo-tube 17 into the longer end 130 of the hub 10. The proximal end of the manifold hypo-tube 17 may be completely inserted into the longer end 130 of the hub 10 until it touches an interior hub 10 wall or, alternatively, until it is located near an interior hub 10 wall. Whether or not the proximal end of the manifold hypo-tube touches an interior wall may be determined by the placement of the bond ports because adhesive injected through the bond ports may be obstructed from reaching the interior surfaces of the manifold hypo-tube if the placement of the manifold hypo-tube 17, within the hub 10, obstructs the bond ports. While the distance that the proximal end of the manifold hypo-tube 17 may be inserted into the hub 10 can vary, it is preferred that the proximal end of the manifold hypo-tube 17 does not touch an interior hub wall 11 so that adhesive injected into the second bond port 15 may flow both inside and outside of the manifold hypo-tube 17. Should the manifold hypo-tube 17 come in contact with the hub wall, adhesive injected through the second bond port 15 may be deterred from traveling completely in and around the proximal end of the manifold hypo-tube 17. Once the proximal end of the manifold hypo-tube 17 is inserted into the hub 10, the proximal or near end of the inner hypo-tube 18, may be placed within the manifold hypo-tube 17 and into the hub 10.

As can be seen in FIG. 1 the proximal end of the inner hypo-tube has a collar 19 adjacent to its tip. This collar may be manufactured from the same material as the liner or any other material compatible with the perishable therapeutic that may be delivered by the device. The collar may be manufactured by extending the lining material, which lines the inner lumen of the inner hypo-tube 18, 0.500 inches past the tip of the inner hypo-tube 18 and, then, by building or wrapping the collar material around the protruding lining material such that, upon completion, the collar is connected to the lumen material and contains an inner lumen of lining material seamlessly connected to the inner hypo-tube. Care should be taken when manufacturing the collar to avoid collapsing the lumen within the liner. Once the collar is manufactured, it should preferably be allowed to cure for 12 hours before it is trimmed. Care should also be taken here, as with the other portions of the assembly process, not to kink, force or otherwise twist the various components. In addition, an assembler should continually verify that no adhesive has entered or has otherwise come in contact with the lumen 101 of the liner 104.

The inner hypo-tube 18 along with collar 19 may then be completely inserted into the hub 10 until the collar 19 comes in contact with the stopping point 120 located within the channel 145 of the hub 10. Once the collar 19 reaches the stopping point 120, an additional axial force may be placed on the inner hypo-tube 18 to further urge or press-fit the collar 19 into the stopping point 120. The collar 19, which may be made from Pebax™ 5533, may be soft and compressible so that it readily deforms under the additional axial load and securely contacts the stopping point 120 to provide a holding force to retain the collar 19 against the stopping point 120.

After the hypo-tubes have been inserted and properly positioned within the longer end 130 of the hub 10 adhesive may be injected into the bond ports. Adhesive may first be injected into the first bond port 14 such that it surrounds the proximal end of the inner hypo-tube 18 and the collar 19 and the adhesive may then be injected into the second bond port to surround the proximal end of the manifold hypo-tube 17. The adhesive injected in the first bond port may cement and lock the inner hypo-tube 18 to the hub 10 and the collar 19 to the tip of the inner hypo-tube 18. It may also provide a bulwark for preventing the unwanted seepage of therapeutic past the collar 19 and down into the larger end 130 of the hub 10. The adhesive may be manufactured by mixing the components by hand for a minimum of 2 minutes to ensure that there is a consistent color in the adhesive. It may then be delivered by placing it in a syringe for injection through the bond ports into the hub.

After adhesive is injected into the first bond port 14 it may be injected into the second bond port 15 to further secure the hypo-tubes to themselves and to the surrounding hub. Excessive adhesive should be removed from the surface of the hub. After the adhesive is allowed to cure, for preferably 12 hours, a 30× microscope may be used to verify a 1mm bond length between the inner hypo-tube 18 and the hub 10 and between the outer hypo-tube 17 and the hub 10.

Figure 2:
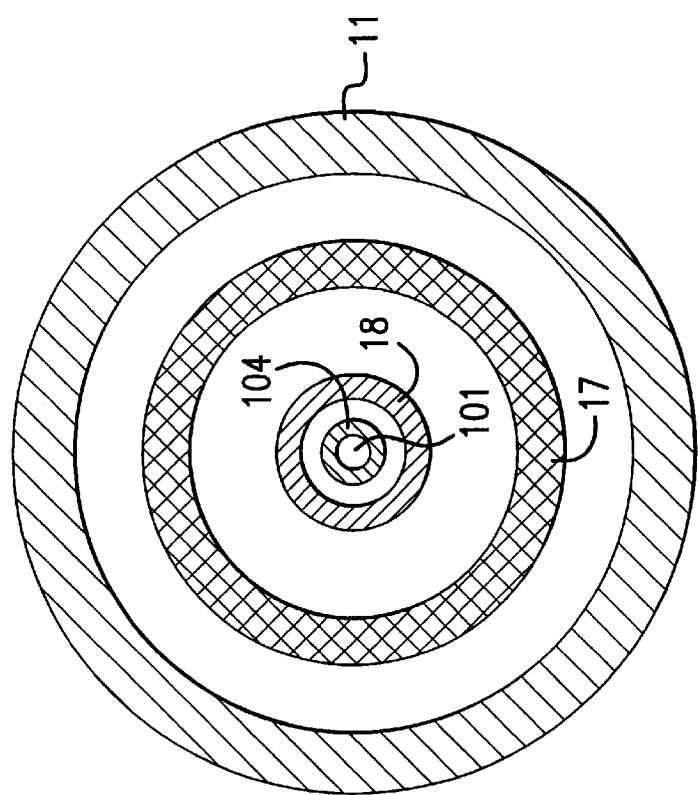
FIG. 2 is a cross-sectional view taken along line 2—2 of FIG. 1.

FIG. 2 is a cross-sectional view taken along line 2—2 of FIG. 1 that illustrates the liner 104, the hub wall 11, the liner lumen 101, the manifold hypo-tube 17, and the inner hypo-tube 18. As can be seen, FIG. 2 illustrates that the longer end 130 of the hub 10 as well as the various lumens and hypo-tubes each have a circular cross-section and that they may be concentrically located about one another. While concentric circular cross-sections are shown in this embodiment other configurations and cross-sections may also be employed. For example, these cross-sections may also be hexagonal, square, and any other cross-section required by the specific application. Moreover, they may not be equally spaced about the same axis but may, instead, be located at different distances from a reference longitudinal axis.

In FIG. 2 the liner 104 is shown as not being in contact with the inner hypo-tube 18, it is preferred, however, that the liner 104 should be in contact with the inner hypo-tube 18 so that the liner 104 may receive structural support from the inside surface of the inner hypo-tube 18 and so that the lumen may have the largest cross-sectional area possible.

FIG. 3 is a sectional view of a cross-section taken along line 3—3 of FIG. 1. As can be seen, the wings 13 protrude outwardly from the hub wall 11 and are aligned 180 degrees from one another. As can also be seen, the collar 19 is in direct contact with the inner surface of the hub wall 11 as well as with the liner 104. It is through this direct contact with the inner surface of the hub that adhesive injected into the hub at bond ports 14 and 15 is prevented from wicking past and into the female luer connection 110 side of the hub 10. Liner lumen 101 is also evident in FIG. 3.

Figure 4:
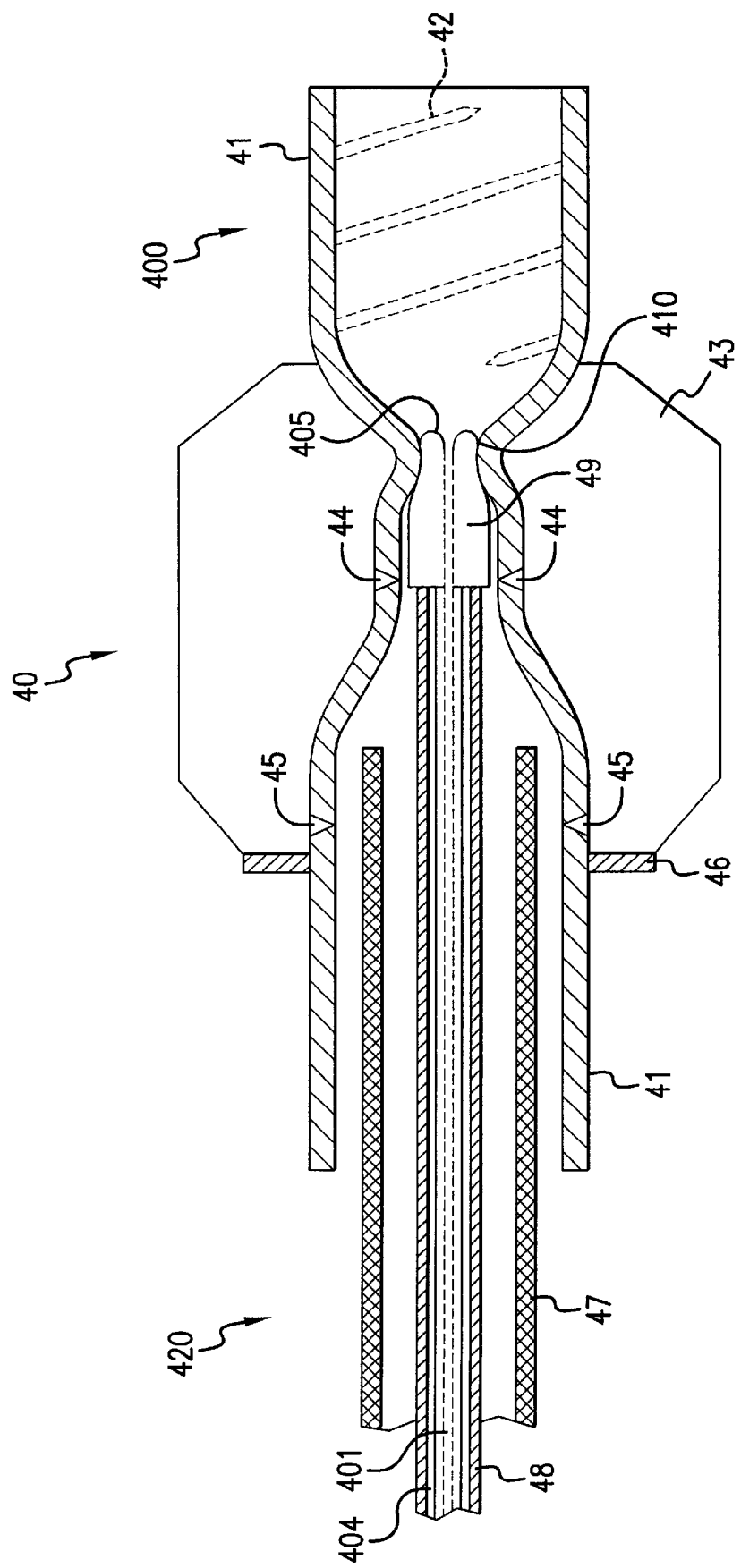
FIG. 4 is a side sectional view of the proximal end of a concentric hypo-tube assembly in accordance with an alternative embodiment of the present invention.

FIG. 4 illustrates a sectional view of an alternative embodiment of the present invention. In FIG. 4 a hub 40 and hypo-tube assembly 420 are shown. The hub 40 has a female luer connection 400 having grooves 42 as well as reinforcing nubs 46, wings 43, a first bond port 44, a second bond port 45, a hub wall 41, and a stopping point 410. The hypo-tube assembly 420 includes a manifold hypo-tube 47, an inner hypo-tube 48, a liner 404, a liner lumen 401, and a collar 49 adjacent to the inner hypo-tube 48. The collar 49 has a heat shrink material 405 placed at its end. This heat shrink material 405 may be made from Teflon™ while the collar may be made from a material that is compatible with a perishable therapeutic, and the hypo-tubes may be made from stainless steel. The hub wall 41 may be homogeneously manufactured from a plastic or other sufficiently rigid material.

As is evident, the proximal end of the inner hypo-tube 48 in this embodiment has been inserted into the hub 40. However, rather than having a silo-shaped collar, as described in the first embodiment, the collar 49 in this embodiment has been covered or otherwise treated with a Teflon™ heat shrink which acts to constrict the outer diameter of the collar and provide a flush and snug fit between the collar 49 and the stopping point 410 of the hub 40.

In order to secure the collar 49 to the hub 40, heat should first be applied to the tip of the collar 49, which contains the Teflon™ heat shrink. The tip of the collar 49 containing the heat shrink will then shrink or constrict under the forces of the heat shrink to a size that closely matches the dimensions of the stopping point 410 of the hub 40. A close dimensional alignment between the tip of the collar 49 and the stopping point 410 will provide a good sealing engagement between the collar and the hub. A benefit of a good sealing engagement is that therapeutic threaded into the female luer connection 400 and injected into the liner lumen 401 will be prevented from passing the interface point between the collar 49 and the stopping point 410 and contacting materials that are not compatible with the therapeutic. To further secure the inner hypo-tube 48 to the stopping point 410, and the other hypo-tube assembly 420 components to the interior of the hub 40, an adhesive should be injected into the first bond port 44 and the second bond port 45 in this embodiment.

Figure 5:
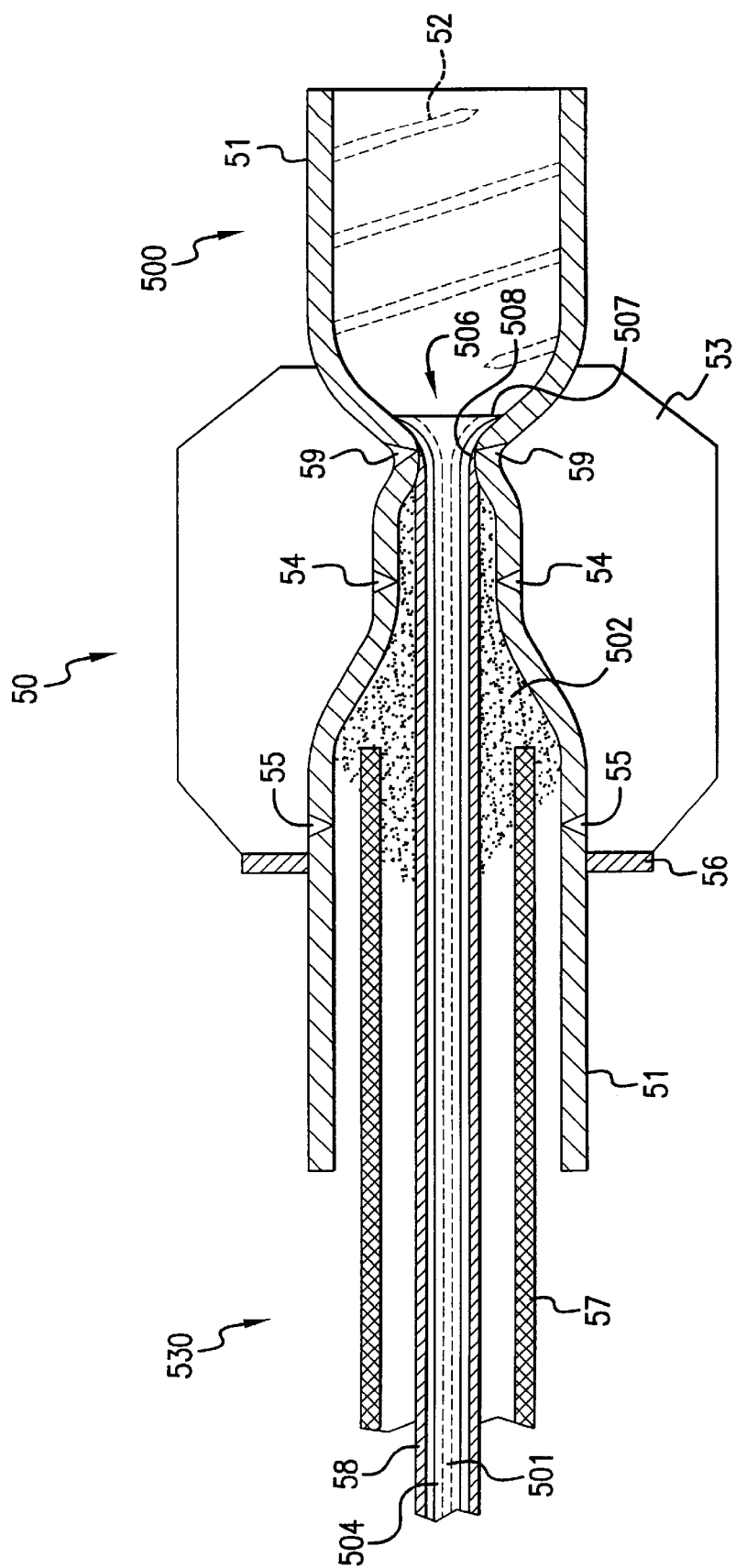
FIG. 5 is a side sectional view of the proximal end of a concentric hypo-tube assembly in accordance with another alternative embodiment of the present invention.

FIG. 5 illustrates a side sectional view of another alternative embodiment of the present invention. Rather than using the collars 19 and 49 described above, the embodiment illustrated in FIG. 5 uses a flared funnel-shaped liner end 506 to facilitate the clean contact and communication between therapeutic placed in the female luer connection 500 and the lumen 501 located within the inner hypo-tube 58.

In FIG. 5 a hub 50 and hypo-tube assembly 530 are illustrated. This hub 50 along with the hypo-tube assembly 530 are shown in sectional view consistent with the illustrations provided in FIGS. 1 and 4 above. This hub 50 contains a hub wall 51, the hub wall 51 having a first bond port 54, a second bond port 55, and a third bond port 59 wherein each bond port is conically shaped and provides a passage from the exterior of the hub 50 to the interior of the hub 50. These bond ports provide access for adhesive to be injected into the hub during the assembly of the device.

Similar to the embodiments described above, the hub wall 51 contains reinforcing nubs 56 and wings 53. These reinforcing nubs 56 and the wings 53 are used to help grasp and secure components to the female luer connection 500 of the hub 50. This female luer connection 500 located at one end of the hub 50 is used to connect other components to the hub 50. This female luer connection 500 contains grooves 52 resident within the inside walls of the female luer connection 500.

Also evident in FIG. 5 are a liner 504, a liner lumen 501, an inner hypo-tube 58, and a manifold hypo-tube 57. In this embodiment, rather than having the collar touch the stopping point of the hub 50 as in the above embodiments, the proximal end of the inner hypo-tube 58 comes in contact with the stopping point 508 of the hub 50 and the liner 501 extends past the end of the inner hypo-tube 58 into the female luer connection 500 of the hub 50. The liner 504 extending into the female luer connection 500 in this embodiment has a liner flared end 506 located at its most proximal end and a liner rim 507. The liner flared end 506 and liner rim 507 extend into the female luer connection 500 and rest up against the hub wall 51. In order to secure this distended liner section to a hub wall 11 adhesive. 502 may be injected behind the liner 504 through the third bond port 59 to secure the liner in place. However, when adhesive is injected into the connection it is preferred that the amount of adhesive is limited such that the adhesive does not wick past the liner rim 507 of the liner 504 and be placed at risk of contacting therapeutic that may be injected into the lumen 501.

In use, when a source of therapeutic is secured or threaded into the female luer connection 500, as the therapeutic is forced down into the lined lumen, the liner flared end 506 and the liner rim 507 may be pressed against the hub wall 51, thereby contributing to a secure and tight contact point between the liner and the hub wall.

Figure 6:
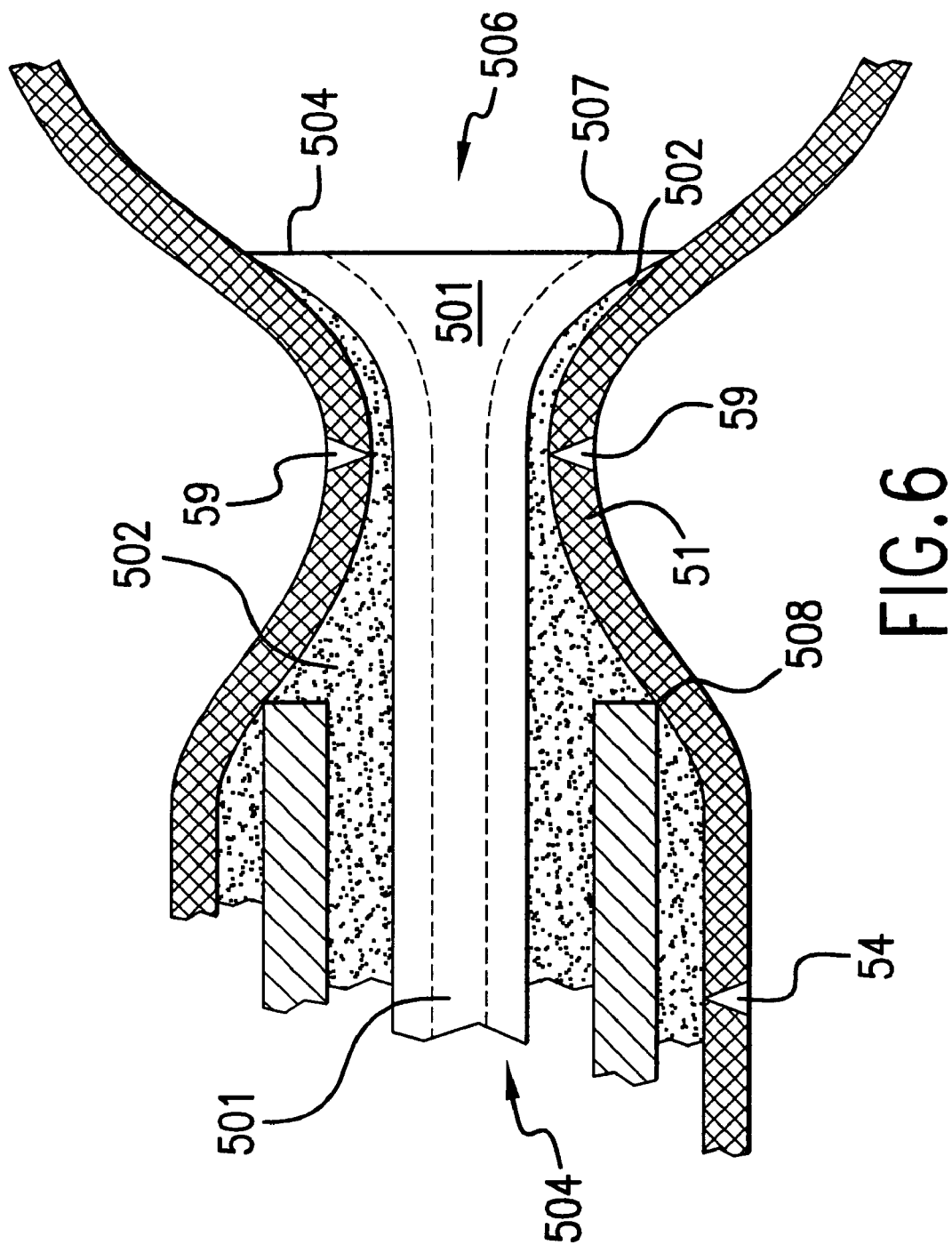
FIG. 6 is an enlarged sectional view of the proximal end of the concentric hypo-tube assembly as employed in the embodiment illustrated in FIG. 5.

FIG. 6 is an enlarged view of the stopping point 508 of the hub 50 from FIG. 5. As is clearly evident in this embodiment adhesive 502 has been injected and is securing the inner hypo-tube rim 508, the liner 504 and the liner flared end 506. As can also be seen, the adhesive 502, while resident in, around, and between the inner hypo-tube, the hub, and the liner 504, does not extend past the liner rim 507. As mentioned above, it is preferable that the adhesive 502 does not extend past the liner rim 507 such that the potential contact between therapeutic and non-compatible materials such as the adhesive 502 may be minimized if not eliminated.

Target sites that may be treated by the various embodiments of the present invention include any mammalian tissue or organ, whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone.

Therapeutics that may be employed in the various embodiments of the present invention include: adenoviral vectors; adeno-associated vectors; certain proteins including basic fibroblast growth factors; certain nucleic acids such as DNA plasmid; and, certain cells such as myoblasts, fibroblasts, and stem cells.

As will be understood by one of skill in the art, while various embodiments of the present invention have been presented, numerous other embodiments are also plausible. For example, rather than having the flared end of the liner protruding into the female luer connection of the hub the liner may instead wrap around and cover the inner hypo-tube rim which is then press-fit into the stopping point of the hub to form a fluid tight connection. Consequently, the disclosed embodiments are illustrative of the various ways in which the present invention may be practiced and other embodiments may be implemented by those skilled in the art without departing from the spirit and scope of the present invention.

What is claimed is:

1. A system for connecting a reservoir of perishable therapeutic with a lumen comprising:
    a hollow hub with an interior surface, the hollow hub having a first end and a second end, the first end in fluid communication with the second end, the second end containing a docking groove, the docking groove sized to couple the reservoir to the second end; and
    an inner hypo-tube, the inner hypo-tube having a proximal tip and an inner lumen, the inner lumen being lined with a perishable therapeutic compatible lining, the inner lumen in fluid communication with the second end through the proximal tip, the lining and the proximal tip configured to shield perishable therapeutic, ejected from the reservoir and present within the second end, from contacting materials that are non-compatible with the therapeutic as the perishable therapeutic enters the inner lumen.

2. The system of claim 1 wherein the proximal tip is in contact with the interior surface of the hub and wherein the lining extends past the proximal tip into the second end and forms a funnel-like shape.

3. The system of claim 1 wherein the proximal tip is in contact with a collar containing a perishable therapeutic compatible material and wherein the collar is in contact with the interior surface of the hub, the collar containing a passage in fluid communication with the inner lumen and the second end.

4. The system of claim 1 further comprising:
a wing, the wing protruding from an outside surface of the hub.

5. The system of claim 4 wherein the wing contains a reinforcing nub formed on the exterior surface of the hub and wherein the exterior surface of the hub is in the shape of an hour-glass.

6. The system of claim 1 wherein the lining covers the proximal tip.

7. The system of claim 1 wherein the first end contains at least one bond port.

8. A system for connecting a reservoir of perishable therapeutic to a lumen lined with a therapeutic compatible liner comprising:
a tubular hub having a first end and a second end, the second end containing a docking groove;
a manifold hypo-tube having a proximal end, the proximal end inserted into the first end of the tubular hub; and
an inner hypo-tube,
the inner hypo-tube having a near end, the near end having a tip,
the inner hypo-tube being lined with a therapeutic compatible liner,
the near end of the inner hypo-tube being located within the proximal end of the manifold hypo-tube, and
the near end of the inner hypo-tube being press-fit into the hub.

9. The system of claim 8 wherein a collar of therapeutic compatible material in contact with the tip of the near end of the inner hypo-tube.

10. The system of claim 8 wherein the therapeutic compatible liner extends out of the near end of the inner hypo-tube and is folded back to cover the tip of the near end of the inner hypo-tube.

11. The system of claim 8 wherein the tubular hub is in the shape of an hour-glass, the first end in communication with the second end through a channel having a diameter smaller than the diameter of the first end and smaller than the diameter of the second end.

12. The system of claim 11 wherein the therapeutic compatible liner extends out of the near end of the inner hypo-tube, through the channel and into the second end of the hub to a liner rim resting against an inner surface of the second end of the hub.

* * * * *